US012579465B2

(12) United States Patent
Passenheim et al.

(10) Patent No.: US 12,579,465 B2
(45) Date of Patent: Mar. 17, 2026

(54) ESTIMATING RELIABILITY OF CONTROL DATA

(71) Applicant: Robert Bosch GmbH, Stuttgart (DE)

(72) Inventors: Simon Passenheim, Berlin (DE); Emiel Hoogeboom, Amsterdam (NL); William Harris Beluch, Stuttgart (DE)

(73) Assignee: ROBERT BOSCH GMBH, Stuttgart (DE)

( * ) Notice: Subject to any disclaimer, the term of this patent is extended or adjusted under 35 U.S.C. 154(b) by 1129 days.

(21) Appl. No.: 17/445,902

(22) Filed: Aug. 25, 2021

(65) Prior Publication Data

US 2022/0101197 A1 Mar. 31, 2022

(30) Foreign Application Priority Data

Sep. 29, 2020 (EP) .................................... 20199055

(51) Int. Cl.
  *G06N 20/00* (2019.01)
  *B25J 9/02* (2006.01)
    (Continued)

(52) U.S. Cl.
  CPC .............. *G06N 20/00* (2019.01); *B25J 9/163* (2013.01); *B25J 9/1671* (2013.01); *B25J 9/023* (2013.01);
    (Continued)

(58) Field of Classification Search
  CPC ......... G06N 20/00; B25J 9/163; B25J 9/1671; B25J 9/023; G05B 2219/40499
  See application file for complete search history.

(56) References Cited

U.S. PATENT DOCUMENTS

| | | | | |
|---|---|---|---|---|
| 7,679,008 B2 * | 3/2010 | Lee | ...................... | H01R 31/065 |
| | | | | 174/521 |
| 7,779,397 B2 * | 8/2010 | Meijer | ...................... | G06F 8/44 |
| | | | | 717/136 |

(Continued)

FOREIGN PATENT DOCUMENTS

| | | |
|---|---|---|
| CN | 110533192 A | 12/2019 |
| CN | 110717600 A | 1/2020 |

(Continued)

OTHER PUBLICATIONS

Driscoll, et al., Computing Fourier Transforms and Convolutions on the 2-Sphere, Advances in Applied Mathematics 15, 202-250. (Year: 1994).*

(Continued)

*Primary Examiner* — Ryan F Pitaro
*Assistant Examiner* — Joseph P Morris
(74) *Attorney, Agent, or Firm* — NORTON ROSE FULBRIGHT US LLP

(57) ABSTRACT

A computer-implemented method of estimating a reliability of control data for a computer-controlled system interacting with an environment. The control data is inferred from a model input by a machine learnable control model which is trained on a training dataset. The model input comprises at least one direction vector which is extracted from sensor data and which is associated with a component of the computer-controlled system or an object in the environment. The reliability is estimated using a generative model that is trained to generate synthetic model inputs representative of the training dataset, by applying an inverse of the generative model to the model input to determine a likelihood of the model input being generated according to the generative model. The generative model comprises a coupling layer (Continued)

comprising a circle transformation and one or more of an unconditional rotation and a conditional rotation.

13 Claims, 5 Drawing Sheets

(51) Int. Cl.
| | | |
|---|---|---|
| *B25J 9/16* | (2006.01) | |
| *G06N 3/0475* | (2023.01) | |
| *G16B 15/20* | (2019.01) | |

(52) U.S. Cl.
CPC .. *G05B 2219/40499* (2013.01); *G06N 3/0475* (2023.01); *G16B 15/20* (2019.02)

(56) References Cited

U.S. PATENT DOCUMENTS

| | | | | |
|---|---|---|---|---|
| 2017/0293859 | A1 | 10/2017 | Gusev et al. | |
| 2018/0322365 | A1* | 11/2018 | Yehezkel Rohekar | ...................... |
| | | | | G06N 3/084 |
| 2019/0294149 | A1* | 9/2019 | Kolouri | ................ G06V 10/764 |
| 2020/0086483 | A1 | 3/2020 | Li et al. | |
| 2020/0110181 | A1 | 4/2020 | Lu et al. | |
| 2020/0257544 | A1* | 8/2020 | Im | ........................ G06F 9/4411 |
| 2021/0019621 | A1* | 1/2021 | Bhattacharyya | ........ G06F 18/25 |
| 2021/0272233 | A1* | 9/2021 | Kondor | .................. G06N 3/045 |
| 2021/0319302 | A1* | 10/2021 | Li | ........................ G06N 3/0464 |

FOREIGN PATENT DOCUMENTS

| | | | | |
|---|---|---|---|---|
| WO | WO-2017168198 | A1 * | 10/2017 | ............. G06F 21/36 |
| WO | 2020166303 | A1 | 8/2020 | |

OTHER PUBLICATIONS

Atanov et al., "Semi-Conditional Normalizing Flows for Semi-Supervised Learning," arXiv:1905.00505v1. (Year: 2019).*

Ziegler et al., "Latent Normalizing Flows for Discrete Sequences," arXiv:1901.10548v4. (Year: 2019).*

Kobyzev et al., "Normalizing Flows: An Introduction and Review of Current Methods," arXiv:1908.09257v4. (Year: 2020).*

Tomczak and M. Welling, "Improving variational auto-encoders using householder flow," arXiv preprint arXiv:1611.09630. (Year: 2016).*

Ingraham, et al., "Generative models for graph-based protein design," 33rd Conference on Neural Information Processing Systems. (Year: 2019).*

N. Jaquier et al. "Bayesian Optimization Meets Riemannian Manifolds in Robot Learning" 3rd Conference on Robotic Leaning, (2019), Osaka, Japan. arXiv:1910.04998v1. 14 Pages.

D. Rezende et al., "Variational Inference with Normalizing Flows" Proceedings of the 32nd International Conference on Machine Learning, Lille, France, 2015. JMLR: W&CP col. 37. 9 Pages.

D. Nielsen et al., "SurVAE Flows: Surjections to Bridge the Gap between VAEs and Flows" arXiv:2007.02731v1, 2020, 26 pages.

D. Rezende et al., "Normalizing Flows on Tori and Spheres" Proceedings of the 37th International Conference on Machine Learning, arXiv:2002.02428v2, Vienna, Austria, PML 119, 2020. 16 Pages.

Kingma and Ba, "Adam: A Method for Stochastic Optimization" ICLR 2015. Retrieved from the Internet on Aug. 23, 2021: https://arxiv.org/abs/1412.6980. 15 Pages.

Amini et al. "Variational Autoencoder for End-to-End Control of Autonomous Driving with Novelty Detection and Training De-Biasing" 2018 IEEE/RS International Conference on Intelligent Robots and Systems, Madrid, Spain, 8 Pages.

Nalisnick et al. "Hybrid Models with Deep and Invertible Features" arXiv:1902.02767v1, 2019, 11 Pages.

* cited by examiner

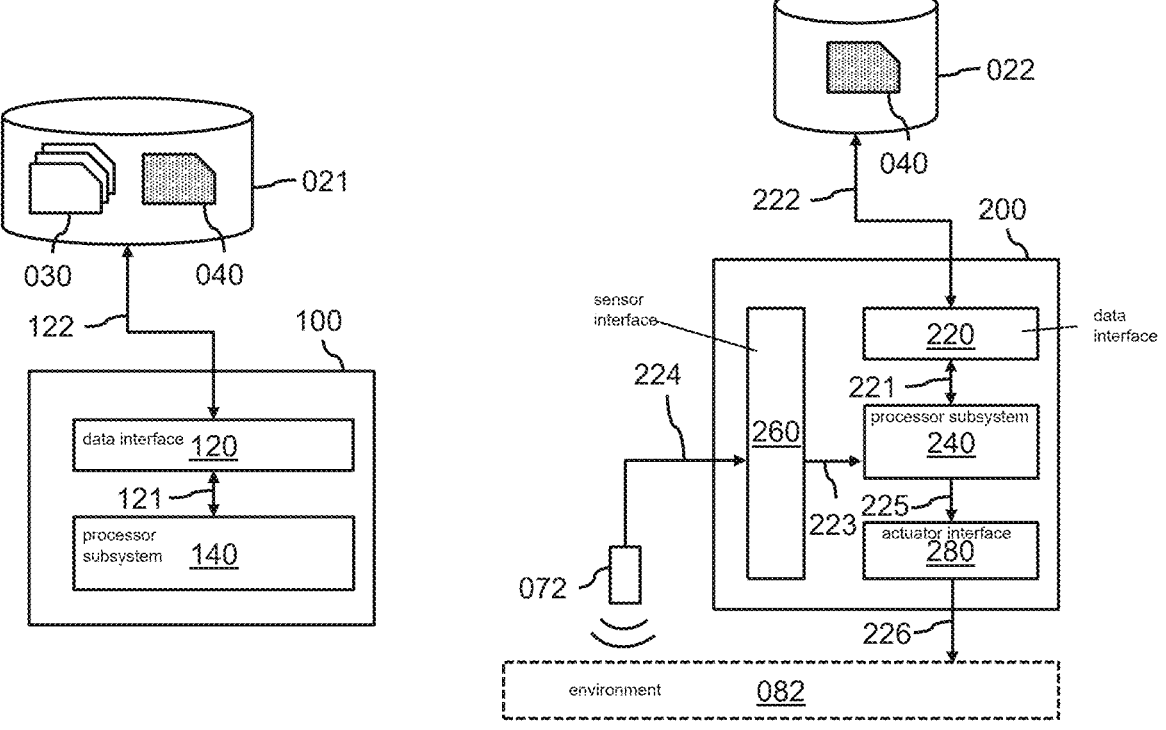
Fig. 1                                                    Fig. 2

ESTIMATING RELIABILITY OF CONTROL DATA

CROSS REFERENCE

The present application claims the benefit under 35 U.S.C. § 119 of European Patent Application No. EP 20199055.3 filed on Sep. 29, 2020, which is expressly incorporated herein by reference in its entirety.

FIELD

The present invention relates to a computer-implemented method of estimating a reliability of control data for a computer-controlled system interacting with an environment, and to a corresponding system. The present invention further relates to a computer-implemented method of generating a synthetic directional data instance, and to a corresponding system. The present invention further relates to a computer-readable medium.

BACKGROUND INFORMATION

Robots (and computer-controlled systems more generally) are more and more being trained automatically to learn new skills or adapt their behaviour to unseen conditions. Since real-world interactions of the robot with its environment are typically costly (and could even be dangerous, if there are humans in the vicinity), it is important to perform such training in a way that is safe, fast, and data-efficient.

In "Bayesian Optimization Meets Riemannian Manifolds in Robot Learning" by N. Jaquier et al. (available at https://arxiv.org/abs/1910.04998 and incorporated herein by reference), a technique for training a robot is provided. The technique is geometry-aware, making use of the fact that parameters representing the robot and/or the environment with which it interacts, are typically not unrestricted independent numerical values, but instead have a geometric meaning. For example, the parameters describing a robot may include one or more orientations or directions, for example, of respective links of a robot arm. Orientations and directions are example of direction vectors that can be represented as point on a (unit) sphere, e.g., a sphere in 4-dimensional space for an orientation or in 3D for a direction. Apart from representing orientations or directions in a computer-controlled system, direction vectors have various other technical uses as described herein, for example, in computational biology.

When deploying a trained computer-controlled system in practice, one of the main challenges is to deal well with unexpected situations. It is typically hard to collect a training set that is representative of the full set of operating conditions that might be encountered in practice. As a consequence, when deployed, the system may end up in a situation that it did not encounter during training. Due to the lack of training examples, there is a danger that the robot performs actions that are harmful, for example, for the robot itself; for the environment with which it interacts (which may for example, in the case of a manufacturing robot, include an object being manufactured); or people who are in the vicinity of the robot. Generally, one way of dealing with such discrepancies between training and use is by performing anomaly detection. Using anomaly detection, the robot may detect that it is in a state that does not conform to the dataset that the robot was originally trained on.

Accordingly, reliability of the trained model in this situation may be expected to be low. Upon such detection the robot may for example be halted, its operation may be switched to a safe mode, or human intervention may be initiated.

SUMMARY

An object of the present invention is to provide techniques for estimating reliability of control data inferred by a machine learnable control model, that provide more accurate results for control data that is inferred from direction vectors, e.g., representing positions or orientations of relevant objects. Using such reliability estimates, the computer-controlled system can be more reliably controlled. Another object of the present invention is to provide techniques for generating synthetic data representative of a training dataset, that provides more accurate results for data that includes direction vectors, e.g., for model inputs to a machine learnable control model. Another object of the present invention is to provide models that can be used both efficiently and accurately both for estimating reliability and for generating synthetic data. Specifically, it is an object to provide an accurate model that is parallelizable and thus can be evaluated for example on a multi-core processor or other parallel execution environments.

In accordance with a first aspect of the present invention, a computer-implemented method and a corresponding system are provided for estimating a reliability of control data. In accordance with another aspect of the present invention, a computer-implemented method and a corresponding system are provided for generating a synthetic directional data instance. In accordance with a further aspect of the present invention, a computer-readable medium is provided. Example embodiments of the present invention are disclosed herein.

Various aspects of the present invention relate to directional data instances, e.g., used as model inputs to a control model. Such a directional data instance may comprise at least one direction vector associated with a physical object. The direction vector may represent a characteristic, or combination of characteristics, of the physical object, that can be represented as a direction, e.g., a point on a hypersphere. For example, the direction vector may represent a direction (e.g., a direction of movement) or an orientation of the object. Here, the term "orientation" is used in the sense of physics, e.g., as an imaginary rotation that is needed (combined with an optional imaginary translation) to move the object from a reference placement to its current placement.

For example, the physical object may be a robot arm, in which case the directional data instance may comprise one or more direction vectors representing orientations of respective links of the robot arm and/or direction vectors representing directions of movement of the respective links. More generally, the physical object may be component of a computer-controlled system or an object in the environment with which the system interacts, e.g., the directional data instance may comprise direction vectors representing direction(s) in the environment used for a path navigation task. As another example, the physical object may be a protein or other biological structure, with the directional data instance representing respective orientations or directions of respective components of the biological structure, e.g., of the backbone of the protein. The directional data instance can for example comprise one or more directions and/or one or more orientations, and/or other direction vectors, for example, at most or at least five, at most or at least ten, or at most or at least twenty direction vectors.

Apart from representing directions associated with the physical object, a directional data instance (e.g., a model input to a control model) typically also represents additional information about the physical object. For example, a direction vector itself may represent not just a direction but also a magnitude, e.g., a speed of movement. In other embodiments, however, a direction vector is used exclusively to represent a direction and not a magnitude. In any case, the directional data instance in many cases comprises additional data apart from the direction vector(s). For example, the directional data instance may represent the state of a robot or other computer-controlled system. Apart from the direction vector(s), such a state may comprise data representing one or more of a force, a torque, a stiffness, an inertia, a manipulability, and a pose of the system or of an object with which it interacts. Generally, the direction vector(s) and/or other data comprised in the direction vector may be extracted from sensor data representing the physical object(s) to which the directional data instance relates.

In various aspects of the present invention, in order to estimate a reliability of a machine learnable control model for such directional data, use is made of a generative model. Generally, the generative model may be trained to generate directional data instances representative of a dataset. The dataset may comprise multiple directional data instances as described above, e.g., extracted from sensor data representing the physical object(s) corresponding to the direction vectors.

In some aspects of the present invention, given a directional data instance, the generative model is used to determine a likelihood of this directional data being generated according to the generative model. In combination with a control model trained on the same dataset, the likelihood may indicate a conformance of the directional data instance to this dataset, and may thus provide an estimate of a reliability of control data that would be inferred from this directional data instance by the control model. In other aspects of the present invention, the generative model is used to generate synthetic directional data instances representative of the dataset. In both cases, it is beneficial for the generative model to generate directional data instance that are more representative of the dataset, e.g., it is beneficial for the generative model to learn a probability distribution over directional data instances that is more representative of the training dataset.

Generally, the generative model may generate a directional data instance from a latent feature vector through the application of one or more trained layers. A layer may transform an input vector to an output vector, e.g., deterministically or stochastically, according to a set of parameters trained when training the generative model. Layers are also known as transformations or mappings. It is conventional to construct generative models by composing layers, and to train such models by log-likelihood optimization, e.g., as described in D. Rezende et al., "Variational Inference with Normalizing Flows" (available at https://arxiv.org/abs/1505.05770 and incorporated herein by reference) and D. Nielsen et al., "SurVAE Flows: Surjections to Bridge the Gap between VAEs and Flows" (available at https://arxiv.org/abs/2007.02731 and incorporated herein by reference). For example, a generative model as described herein may be implemented as a normalizing flow or a SurVAE flow. As a consequence, for example, the generative model may allow exact likelihood evaluation, efficient inference/data synthesis and latent space representation learning useful for downstream tasks.

Interestingly, generative models described herein use a coupling layer that is specifically designed to accurately represent transformations on directional data. The coupling layer transforms an input direction vector to an output direction vector. The coupling layer may map an input direction vector lying on a hypersphere to an output direction vector lying on that same hypersphere, e.g., the coupling layer may represent a norm-preserving mapping. Thus, the coupling layer may act on the direction represented by the input direction vector.

For example, the input direction vector and/or the output direction vector may represent a direction in 3D (e.g., as a point on the 3-dimensional sphere $\mathbb{S}^2$), an orientation in 3D (e.g., as a point on the hypersphere $\mathbb{S}^3$), or a concatenation of multiple such directions and orientations. The coupling layer may act on the input direction vector, leaving other elements of the representation of the directional data instance unchanged.

In order to transform the input direction vector to the output direction vector, the coupling layer may apply an unconditional rotation and/or a conditional rotation to the input direction vector. The unconditional rotation may rotate the input direction vector (or the result of applying a transformation of the coupling layer to the input direction vector) according to parameters of the generative model. The conditional rotation may rotate a first subset of Cartesian coordinates of the input direction vector (or the result of applying a transformation of the coupling layer) based on another set of Cartesian coordinates of this vector, disjoint from the first subset, e.g., the remaining coordinates. For example, in k-dimensional space, a rotation may correspond to a multiplication by a SO(k) matrix. The rotation may be norm-preserving. Generally, the conditional and/or unconditional rotations can be deterministic or stochastic.

Apart from the unconditional and/or conditional rotation, the coupling layer may further comprise circle transformations that act independently on one or more circle slices, e.g., pairs of Cartesian coordinates, of the input direction vector (e.g., with rotations(s) already applied to this vector). Generally, such a pair of Cartesian coordinates represents a point on a circle with a certain radius (which need not be one). The circle transformation may transform the point on that circle, to another point on that same circle (e.g., same point if the transformation is the identity for that particular point). For example, parameterizing the point by an angle and radius, the circle transformation may transform the angle but not the radius. Also the circle transformation can be deterministic or stochastic. Interestingly, as a consequence of preserving the radius of the circle corresponding to the pair of Cartesian coordinates, also the radius of the overall direction vector being transformed may be preserved.

The circle transformation may be parameterized, e.g., by parameters of the generative model and/or further Cartesian coordinates that do not correspond to the circle slice. Preferably, the circle transformation is an invertible function with an invertible inverse, e.g., a diffeomorphism. Respective circle transformations may be applied to respective, preferably pairwise disjoint, pairs of Cartesian coordinates, for example, to each pair of Cartesian coordinates of the subset to which a conditional rotation was applied. The circle transformation may be parameterized based on coordinates unaffected by the conditional rotation.

The inventors found that use of a coupling layer that combines rotations and circle transformations as described, allows to represent a wide range of transformations on directional data. Rotation is a particularly natural and important transformation to be applied to directional data, so applying it conditionally and/or unconditionally is particularly useful. Interestingly, by combining this with transformations of circle slices, also functionality can be realized that does not correspond to a higher-dimensional rotation. Still, by construction, the norm of the transformed direction vector may be preserved, and accordingly, a flexible and powerful transformation on direction vectors is obtained. In various embodiments, the generative model combines multiple coupling layers in parallel and/or in sequence, allowing to flexibly learn more complex transformations, inducing more complex probability distributions over the generated directional data. Thus, anomalies in measured directional data can be more accurately detected, and synthetic directional data instance that are more representative of previously measured directional data instances can be generated, for example.

One important advantage of the use of rotations and circle transformations is that it allows the coupling layer to be used not only in the generative direction, e.g., to generate synthetic directional data; but also in the inverse direction, sometimes referred to as the inference direction. For example, the inverse of the coupling layer may be efficient and accurate to compute, e.g., allowing to compute an exact inverse without the need for stochastic approximations or numerically stable inversion techniques.

In particular, since respective circle transformations may act independently on respective pairs of Cartesian coordinates, the inverse of the generative model may be computed by separately inverting respective circle transformations. A circle transformation may be parameterized based on other coordinates and model parameters. Interestingly, since these values are not affected by the transformation, these parameters can be computed from the output of the circle transformation in the same way that they are computed from the input of the circle transformation. Moreover, the independent transformation of circle slices may result in a Jacobian that has a triangular structure and that can thus be inverted in an accurate, efficient, and numerically stable way. The inverse Jacobian may be used for log-likelihood computations. Thus, use of the generative model in the inference direction is improved.

Similarly, since the conditional rotation acts on a subset of Cartesian coordinates parameterized based on other coordinates and/or model parameters, and these values are also not affected by the conditional rotation, also the parameters that were used in the conditional rotation can be determined from its output in the same way that they are computed from its input. Moreover, conditional and unconditional translation can be efficiently inverted since their inverses are translations as well.

Accordingly, through the way that the coupling layer is constructed using rotations and circle transformations, it is possible to perform both density evaluation (as used for determining conformance, and for training the generative model) and sampling (as used for generating synthetic directional data) efficiently and accurately. In particular, it can be avoided to use an iterative procedure based on autoregressive flows, which has increased computational complexity for high dimensional data, and which has the property that density evaluation and sampling from the model density cannot be done efficiently at the same time (e.g., an autoregressive flow either goes from uniform space to model data space or the other way round, and depending on the choice, either sampling or density evaluation may be inefficient).

Another advantage of the presented coupling layer that contributes towards its improved accuracy, is that singularities can be avoided. For example, a trainable mapping on hyperspheres is described in D. Rezende et al., "Normalizing Flows on Tori and Spheres" (available at https://arxiv.org/abs/2002.02428 and incorporated herein by reference) which makes use of cylinders. However, since the cylinder and the sphere are topologically not equivalent, the mapping between the two is not diffeomorphic, and in particular, there are singularities e.g. at polar points.

Interestingly, using the coupling layer presented herein allows to avoid such singularities. For example, a diffeomorphic map and thus a continuous model density may be obtained. In particular, reliability close to such singularities is improved. This is particularly important when determining conformance, since this is exactly meant to deal with exceptional situations reliably.

Optionally, applying a circle transformation may comprise mapping a pair of Cartesian coordinates to an angle; applying a circle diffeomorphism to the angle; and mapping the angle to Cartesian coordinates. Similarly, the inverse of the circle transformation may be applied by mapping the Cartesian coordinates to the angle, applying the inverse of the circle diffeomorphism, and mapping the result back to Cartesian coordinates. This helps to guarantee that the resulting circle transformation is invertible. This is more complex to guarantee, e.g., for functions acting directly on the 2-D plane. Also a likelihood contribution for the circle transformation can be efficiently computed based on likelihood contributions of the mappings between angles and coordinates; and of the circle diffeomorphism.

Optionally, the circle diffeomorphism may be parameterized according to a trained parameter model, e.g., a neural network or the like. As its inputs, the parameter model may use the size of the circle, and/or Cartesian coordinates to which no circle transformation is applied. For example, the Cartesian coordinates of the direction vector may be partitioned into one or more sets of pairs, and a set of remaining Cartesian coordinates. In such a case, the circle transformation may be applied to the respective pairs with parameters being determined by evaluating the trained parameter model using the size of the circle and/or one, more, or all of the remaining coordinates. Only using Cartesian coordinates to which no circle transformation is applied by the coupling layer, has the advantage that respective circle transformations can be evaluated in parallel, since the computation of parameters for one circle transformation does not require the transformation of another circle slice to have already been performed.

Optionally, the unconditional rotation and/or the conditional rotation may be implemented by using multiple Householder reflections. Householder reflections allow both the rotation and its inverse to be efficiently implemented. Accordingly, better results may be obtained compared to working with rotation angles, for example. In various embodiments of the present invention, the number of Householder reflections is chosen equal to the dimension of the vector to which they are applied, e.g., the overall direction vector or the subset of coordinates to which the conditional rotation is applied. This in principle allows any rotation to be represented. However, it is also possible to use fewer Householder reflections, which may result in a more data-efficient model, e.g., may reduce overfitting.

Optionally, a direction vector of a directional data instance may represent an orientation of a physical object in three-dimensional space. Such an orientation may be represented by a unit quaternion, e.g., by four real values with sum of squares equal to one. In some embodiments of the present invention, the input and output direction vectors of a coupling layer may each represent one orientation. In some embodiments of the present invention, the input and output direction vectors of a coupling layer may comprise multiple unit quaternions, e.g., may represent a concatenation of multiple orientations, for example, two, three, at most or at least five, or at most or at least ten orientations.

In various aspects, the generative model is used to estimate reliability of control data inferred by a machine learnable control model from a model input. This reliability may be estimated based on a conformance of the model input to the training dataset of the control model. To this end, the model input may be obtained, e.g., the model input may be extracted from sensor data, e.g., by determining directions and/or orientations of physical objects, e.g., components of the system to be controlled or objects in its environment. For example, the sensor data may be image or video data capturing the physical objects.

To determine conformance of the model input to the training dataset, or of a directional data instance to a dataset more generally, an inverse of the generative model may be applied to the obtained directional data instance to determine a likelihood (e.g., a log-likelihood) of the directional data instance being generated according to the generative model. This typically involves applying an inverse of the coupling layer, e.g., obtaining an output direction vector and using the inverse to determine a corresponding input direction vector (e.g., deterministically if the inverse is deterministic or by sampling if the inverse is stochastic). Determining the likelihood may involve determining a determinant of an inverse of a Jacobian or other type of likelihood contribution for the coupling layer, as is conventional for normalizing flows or SurVAE flows. Interestingly, by the construction of the coupling layer, exact likelihood estimation may be enabled.

Based on the determined likelihood, a conformance value may be output indicating a conformance of the directional data instance to the dataset on which the generative model was trained. For example, if the dataset is a training dataset of a further machine learnable model, the conformance value may be used as a reliability measure for the directional data instance as a model input for the further machine learnable model. For example, the log-likelihood itself may be output, or a value derived from it such as a binary label. Because of the use of the coupling layer as described herein, the generative model better represents the dataset and thus, a more accurate conformance value is obtained.

Optionally, a direction vector may represent an orientation of a link of a robot arm; for example, the directional data instance may comprise multiple such direction vectors representing respective orientations. The determined conformance value may be used as a reliability measure of a control model for controlling the robot arm, for example, by operating the robot in a safe mode or halting it in case the conformance value indicates non-conformance. For example, directional data instances in the dataset may represent normal states of the robot and/or its environment, non-conformance indicating an exceptional situation for which appropriate action needs to be taken.

Optionally, the control model or other further machine learnable model may be applied to the directional data instance at least if the reliability measure indicates sufficient reliability. The conformance value may be used to decide how to use the model output of the further machine learnable model, e.g., to discard it or not, or to assign it a higher or lower weight, etc. For example, the model output may be discarded, and/or an alert may be raised, if the log-likelihood is below a threshold. If the model output is sufficiently reliable, the computer-controlled system may be controlled according to it.

A robotic system is an example of such a computer-controlled system; for example, this can be a robot arm as described before, but various other types of robots are possible as well and also involve directional data, e.g., drones or humanoids. For example, the robot can perform one or more tasks automatically, e.g., under control of an external device or an embedded controller. Further examples of computer-controlled systems to which the described techniques can be applied, are vehicles and components thereof, domestic appliances, power tools, manufacturing machines, personal assistants, access control systems, drones, nanorobots, and heating control systems.

Optionally, a synthetic directional data instance generated by the generative model, or a directional data instance to which the inverse of the generative model is applied, may represent a protein or other biological structure. For example, the directional data instance may represent a candidate protein conformation. In particular, the direction vector in this case may represent an orientation or a direction of a component of the protein or other biological structure. Using the generative model, a candidate protein conformation may be generated. This candidate may then be checked, automatically and/or manually, for validity, for example, by using an energy function as is conventional. It is also possible to use the inverse of the generative model to check a candidate that is otherwise generated for conformance to a dataset of valid conformations, e.g., instead of or in addition to other validity checks. In either case, if found valid, the protein may be automatically synthesized, for example.

Optionally, the generative model may be used to train the generative model based on the training dataset. In this case, directional data instances may be obtained by retrieving them from a training dataset. The inverse of the generative model may be used to determine a likelihood for a directional data instance from the training dataset, and the determined likelihood may be maximized. Accordingly, a generative model may be obtained that represents the training dataset.

In various aspects, the generative model is applied to generate synthetic directional data instances according to the generative model. Because the generative model comprises the coupling layer as described herein, the generated instances more accurately represent the dataset on which the generative model was trained.

Optionally, the generative model may be applied repeatedly to obtain multiple generated directional data instances. The multiple directional data instances may be used as training and/or test data in training a further machine learnable model, for example, a control model for a computer-controlled system. The synthetic data may be used for data augmentation, e.g., in order to train the further machine learnable model on larger datasets and/or data of situations for which it is hard to obtain training data, e.g., dangerous or rare situations of a computer-controlled system interacting with its environment. For example, the generated data may be manually or automatically labelled, or the further machine learnable model may be trained in an unsupervised way. By using the synthetic data, a better-trained machine learnable model may be obtained without the need to perform further real physical measurements and/or interactions.

Optionally, an input instance to the further machine learnable model may be obtained, and the further machine learnable model may be applied to the input instance to determine an output of the further machine learnable model. For example, the output may be used as control data in controlling a computer-controlled system. Because the further machine learnable model is trained on better training data, also the quality of its resulting outputs is improved, e.g., controlling of the system is improved.

It will be appreciated by those skilled in the art in view of the disclosure herein that two or more of the above-mentioned embodiments, implementations, and/or optional aspects of the present invention may be combined in any way deemed useful.

Modifications and variations of any system and/or any computer readable medium, which correspond to the described modifications and variations of a corresponding computer-implemented method, can be carried out by a person skilled in the art on the basis of the present description.

BRIEF DESCRIPTIONS OF DRAWINGS

These and other aspects of the present invention are apparent from and will be elucidated with reference to the embodiments of the present invention described hereinafter.

FIG. 1 shows a system for training and/or using a generative model, in accordance with an example embodiment of the present invention.

FIG. 2 shows a system for estimating reliability of control data, in accordance with an example embodiment of the present invention.

Figure 3:
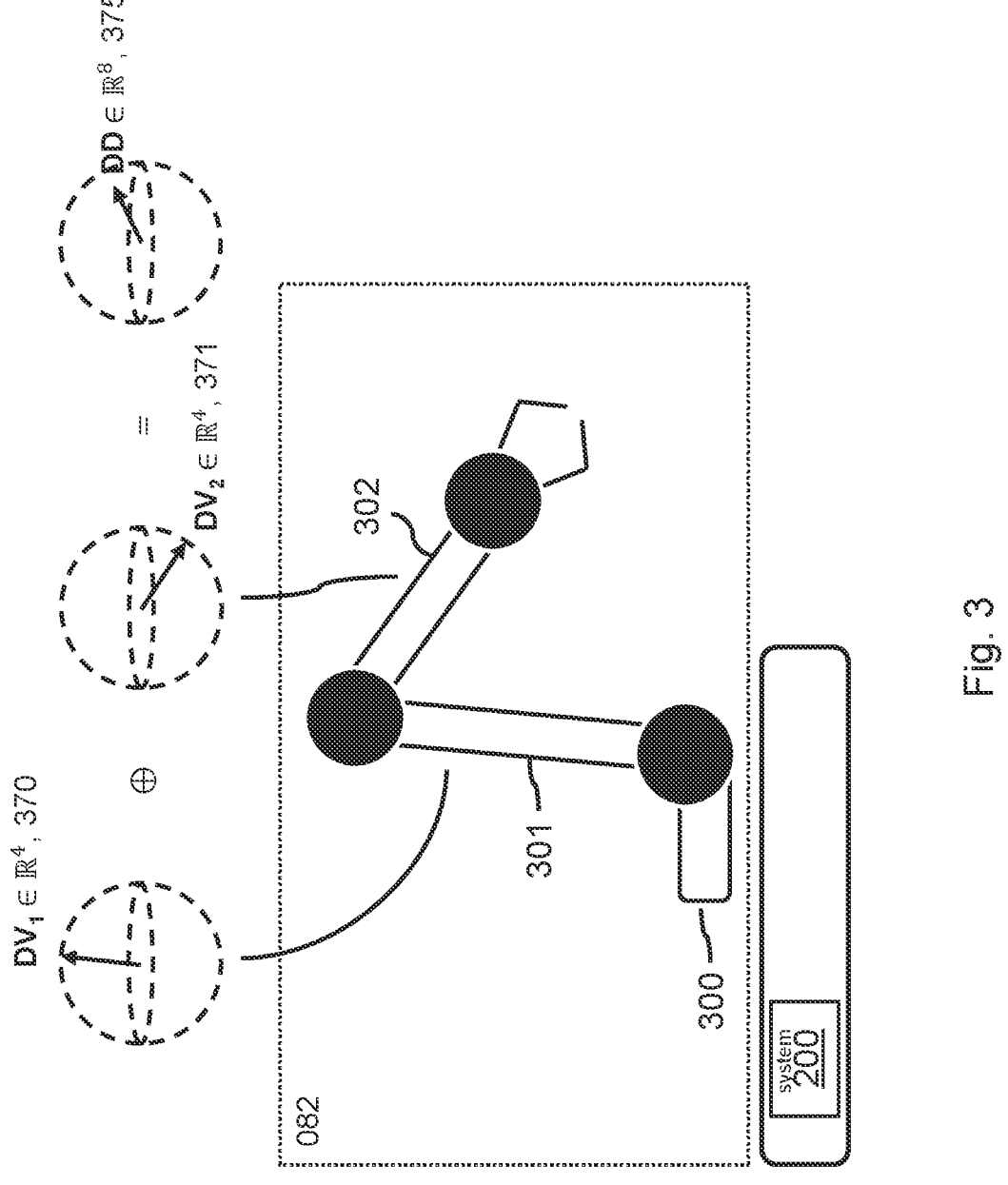
FIG. 3 shows a system for estimating reliability of control data of a robot arm, in accordance with an example embodiment of the present invention.

It should be noted that items which have the same reference numbers in different Figures, have the same structural features and the same functions, or are the same signals. Where the function and/or structure of such an item has been explained, there is no necessity for repeated explanation thereof in the detailed description.

DETAILED DESCRIPTION OF EXAMPLE EMBODIMENTS

FIG. 1 shows a system 100 for training a generative model 040 and/or generating a synthetic directional data instance according to the generative model 040.

The system 100 may comprise a data interface 120 for accessing model data 040 representing the generative model. Generally, the model data 040 may comprise parameters for evaluating the model in the generative direction, e.g., to generate synthetic directional data instances, and/or parameters for evaluating the model in the inference direction, e.g., parameters of an inverse of the generative model, e.g., to determine conformance to a dataset.

For example, the parameters may comprise parameters of one or more neural networks, e.g., of parameter determining models for transformations of coupling layers. Neural networks are also known as artificial neural networks. Examples include deep neural networks and convolutional neural networks. In this case, the set of parameters may comprise weights of nodes of the neural network. The parameters may also comprise parameters of probability distributions used in a coupling layer, etc. Depending on the particular application, various conventional architectures for neural networks and other types of machine learnable models may be used.

The parameters for the generative and inference directions typically overlap but do not need to coincide. For example, a transformation of the generative model may be deterministic in one direction and stochastic in the other, in which case the number of parameters for the stochastic direction is typically larger. For example, the number of parameters for the generative direction and/or for the inference direction may be at least 10000, at least 100000, or at least 1000000.

The generative model may be trained by system 100, or may have been previously trained, on a training dataset. In both cases, a directional data instance from the training dataset may comprise at least one direction vector associated with a physical object extracted from sensor data representing the physical object.

In case system 100 applies generative model 040 based on a generative model that was previously trained on a training dataset, the model data 040 accessed by the system may comprise just the parameters for the generative direction, e.g., not the parameters for the inference direction. In case system 100 trains the generative model on a training dataset, the model data 040 typically comprises parameters for both the generative and the inference direction.

In case system 100 trains the generative model, the data interface may also be for accessing the training dataset 030 on which the model is trained. For example, the training dataset may comprise at least 100, at least 10000, or at least 1000000 directional data instances. Accordingly, data interface 120 may act as an input interface for obtaining directional data instances for training the generative model from the training dataset 030. The generative model trained by system 100 may be for generating synthetic directional data instances according to a method described herein, e.g., by system 100 itself or by a different instance of the system of FIG. 1 that is configured to generate directional data instances according to the model but not to train it. Instead or in addition, the generative model trained by system 100 may be for determining conformance of a directional data instance according to a method described herein, for example as a reliability measure of a control model, e.g., by system 200 of FIG. 2.

As also illustrated in FIG. 1, the input interface may be constituted by a data storage interface 120 which may access the data 030, 040, from a data storage 021. For example, the data storage interface 120 may be a memory interface or a persistent storage interface, e.g., a hard disk or an SSD interface, but also a personal, local or wide area network interface such as a Bluetooth, Zigbee or Wi-Fi interface or an ethernet or fiberoptic interface. The data storage 021 may be an internal data storage of the system 100, such as a hard drive or SSD, but also an external data storage, e.g., a network-accessible data storage. In some embodiments, the data 030, 040 may each be accessed from a different data storage, e.g., via a different subsystem of the data storage interface 120. Each subsystem may be of a type as is described above for the data storage interface 120.

The system 100 may further comprise a processor subsystem 140. Processor subsystem 140 may be configured to, during operation of the system 100, train the generative model 040 by maximizing a determined likelihood for directional data instances from dataset 030. The likelihood may be determined by processor subsystem 140 by applying an inverse of the generative model to the directional data instance to determine a likelihood of the directional data instance being generated according to the generative model. The training may comprise outputting the likelihood as a conformance value indicative of a conformance of the directional data instance to the dataset, and using the likelihood as a training signal for training the generative model 040.

The generative model may generate the directional data instance by transforming an input direction vector to an output direction vector according to a coupling layer.

As part of applying the inverse of the generative model, processor subsystem 140 may be configured to apply an inverse of this coupling layer. This may comprise applying an inverse of a circle transformation. This inverse may be applied to a pair of Cartesian coordinates representing a point on a circle. This inverse may transform said point to a further point on the circle. The circle transformation may be defined based on parameters of the generative model and/or further Cartesian coordinates. Applying the inverse of the coupling layer may further comprise applying an inverse of an unconditional rotation and/or of a conditional rotation. The inverse of the unconditional rotation may rotate a direction vector according to parameters of the generative model. The inverse of the conditional rotation may rotate a first set of Cartesian coordinates based on a second set of Cartesian coordinates.

Instead of or in addition to training the generative model, processor subsystem 140 may be configured to, during operation of the system 100, apply the generative model 040 to generate a synthetic directional data instance. This applying may comprise applying the coupling layer to an input direction vector. The applying of the coupling layer may comprise applying an unconditional rotation and/or a conditional rotation. The unconditional rotation may rotate a direction vector according to parameters of the generative model. The conditional rotation may rotate a first set of Cartesian coordinates based on a second set of Cartesian coordinates. The applying of the coupling layer may further comprise applying a circle transformation to a pair of Cartesian coordinates representing a point on a circle. This transformation may transform said point to a further point on the circle. The circle transformation may be defined based on parameters of the generative model and/or further Cartesian coordinates.

The system 100 may further comprise an output interface. The output interface may be for outputting trained data representing the learned (or 'trained') model, and/or for outputting a generated synthetic directional data instance or data based on it.

For example, processor subsystem 140 may be configured to, during operation of system 100, apply the generative model repeatedly to obtain multiple generated directional data instances, and to train a further machine learnable model (e.g., a control model) using the multiple directional data instances as training and/or test data. The further machine learnable model may be output using the output interface. Instead or in addition, a model input to the further machine learnable model may be obtained, and the further machine learnable model may be applied to the model input to determine an output (e.g., control data) of the further machine learnable model, with the output of the further machine learnable model being output by the output interface.

For example, as also illustrated in FIG. 1, the output interface may be constituted by the data interface 120, with said interface being in these embodiments an input/output ('IO') interface, via which the output data may be stored in the data storage 021. For example, the model data 040 defining the 'untrained' model may during or after the training be replaced, at least in part, by the model data of the trained model, in that the parameters of the model, such as weights and other types of parameters of neural networks, may be adapted to reflect the training on the training data 030. This is also illustrated in FIG. 1 by same reference numeral 040 being used to refer to both the untrained and the trained model data. In other embodiments, the trained model data may be stored separately from the model data defining the 'untrained' model.

In some embodiments, the output interface may be separate from the data storage interface 120, but may in general be of a type as described above for the data storage interface 120. In case control data is output, the output interface can also be an actuator interface e.g. as discussed with respect to FIG. 2.

FIG. 2 shows a system 200 for determining conformance of a directional data instance to a dataset. In this example, the directional data instance is a model input to a machine learnable control model for controlling a computer-controlled system. The conformance may provide an estimate of a reliability of the machine learnable control model for the model input. The system 200 may be a control system which controls the computer-controlled system. The system 200 may train the generative model in addition to applying it, e.g., may be combined with the system of FIG. 1.

The system 200 may comprise a data interface 220 for accessing trained model data 040 representing a trained generative model as may be generated by the system 100 of FIG. 1 or as described elsewhere. The generative model may be trained to generate directional data instances representative of the dataset. This generating may comprise transforming an input direction vector to an output direction vector according to a coupling layer. As also discussed with respect to FIG. 1, the model data 040 may comprise at least parameters needed to apply the generative model in the inference (inverse) direction, but need not comprise additional any parameters needed to apply the generative model in the generative direction.

For example, as also illustrated in FIG. 2, the data interface may be constituted by a data storage interface 220 which may access the data 040 from a data storage 022. In general, the data interface 220 and the data storage 022 may be of a same type as described with reference to FIG. 1 for the data interface 120 and the data storage 021. Although not shown in the figure, the data interface may also be for accessing model data representing the machine learnable control model.

The data interface may also act as an input interface for obtaining a directional data instance to be used as a model input for the further machine learnable control model. The directional data instance may comprise at least one direction vector associated with a physical object, e.g., a component of the computer-controlled system or an object in the environment of the computer-controlled system. The direction vector may have been previously be extracted from sensor data representing the physical object. This figure illustrates the case where the input interface is a sensor interface 260, wherein the directional data instance 223 is extracted from sensor data 224 by the sensor interface 260, as discussed in more detail below. The directional data instance can also be obtained via another type of input interface.

The system 200 may further comprise a processor subsystem 240 which may be configured to, during operation of the system 200, apply an inverse of the generative model 040 to the directional data instance 223 to determine a likelihood of the directional data instance being generated according to the generative model. Based on said likelihood, processor subsystem 240 may output a conformance value indicative of a conformance of the directional data instance to the dataset, and thus in this case estimating a reliability of control data that would be inferred by the machine learnable control model using the directional data as a model input.

This applying may comprise applying an inverse of the coupling layer. Applying the inverse of the coupling layer may comprise applying an inverse of a circle transformation. This inverse may be applied to a pair of Cartesian coordinates representing a point on a circle. This inverse may transform said point to a further point on the circle. The circle transformation may be defined based on parameters of the generative model and/or further Cartesian coordinates. Applying the inverse of the coupling layer may further comprise applying an inverse of an unconditional rotation and/or of a conditional rotation. The inverse of the unconditional rotation may rotate a direction vector according to parameters of the generative model. The inverse of the conditional rotation may rotate a first set of Cartesian coordinates based on a second set of Cartesian coordinates.

It will be appreciated that the same considerations and implementation options apply for the processor subsystem 240 as for the processor subsystem 140 of FIG. 1. It will be further appreciated that the same considerations and implementation options may in general apply to the system 200 as for the system 100 of FIG. 1, unless otherwise noted.

FIG. 2 further shows various optional components of the system 200. For example, in some embodiments, the system 200 may comprise a sensor interface 260 for directly accessing sensor data 224 acquired by a sensor 072 in an environment 082. A direction vector of the directional data instance 223, associated a physical object of the computer-controlled system or its environment 082, may be extracted from the sensor data 224. The sensor may be arranged in environment 082 but may also be arranged remotely from the environment 082, for example if the quantity(s) can be measured remotely. The sensor 072 may but does not need to be part of the system 200. The sensor 072 may have any suitable form, such as an image sensor, a lidar sensor, a radar sensor, a pressure sensor, a temperature sensor, etc. The sensor interface 260 may have any suitable form corresponding in type to the type of sensor, including but not limited to a low-level communication interface, e.g., based on I2C or SPI data communication, or a data storage interface of a type as described above for the data interface 220.

In some embodiments of the present invention, the system 200 may comprise an actuator interface 280 for providing control data 226 to an actuator (not shown) in the environment 082. The control data 226 may be generated by the processor subsystem 240 to control the actuator based on the determined conformance value, e.g., by using the conformance value to decide whether or not to use the control data of the machine learnable control model, e.g., the control data of the model may be used only if sufficiently reliable. The actuator may be part of system 200. For example, the actuator may be an electric, hydraulic, pneumatic, thermal, magnetic and/or mechanical actuator. Specific yet non-limiting examples include electrical motors, electroactive polymers, hydraulic cylinders, piezoelectric actuators, pneumatic actuators, servomechanisms, solenoids, stepper motors, etc. Such type of control is described with reference to FIG. 3 for a robotic system.

In other embodiments (not shown in FIG. 2), the system 200 may comprise an output interface to a rendering device, such as a display, a light source, a loudspeaker, a vibration motor, etc., which may be used to generate a sensory perceptible output signal which may be generated based on the determined reliability measure, e.g., a control signal inferred by the machine learnable control model may be output along with the determined reliability measure.

In general, each system described in this specification, including but not limited to the system 100 of FIG. 1 and the system 200 of FIG. 2, may be embodied as, or in, a single device or apparatus, such as a workstation or a server. The device may be an embedded device. The device or apparatus may comprise one or more microprocessors which execute appropriate software. For example, the processor subsystem of the respective system may be embodied by a single Central Processing Unit (CPU), but also by a combination or system of such CPUs and/or other types of processing units. The software may have been downloaded and/or stored in a corresponding memory, e.g., a volatile memory such as RAM or a non-volatile memory such as Flash. Alternatively, the processor subsystem of the respective system may be implemented in the device or apparatus in the form of programmable logic, e.g., as a Field-Programmable Gate Array (FPGA). In general, each functional unit of the respective system may be implemented in the form of a circuit. The respective system may also be implemented in a distributed manner, e.g., involving different devices or apparatuses, such as distributed local or cloud-based servers. In some embodiments, the system 200 may be part of vehicle, robot or similar physical entity, and/or may be represent a control system configured to control the physical entity.

FIG. 3 shows an example of the above, in that the system 200 is part of a robotic system together with a robot arm 300, the system being used as a control system to control the robot arm 300. Although a robot arm is used as an example, the skilled person understands that the system can also control another type of computer-controlled system, such as a (semi-)autonomous vehicle, a building control system, etc.

The robot arm 300 may act in an environment 082, e.g., as part of a manufacturing pipeline. The robot arm in this figure, as an illustrative example, has two links 301, 302. Other numbers of links, e.g., one, three, or at least four, are also possible. Controlling the robot arm 300 may comprise controlling the connections between links of the robot arm to move the robot arm in a given direction.

For example, in normal operation, system 200 may control the robot arm 300 according to a machine learnable control model, e.g., a policy trained using reinforcement learning based on a training dataset. The machine learnable control model may take as a model input directional data instance DD, 375, including directional vectors DV1, 370, DV2, 371, indicating orientations of links 301, 302 of the robot arm. The directional data instance DD may comprise additional data, e.g., measured forces, torques, etc.

It may be challenging in this setting to collect training data on exceptional cases. Thus, in these exceptional cases, the further machine learnable model may be expected to be less reliable. At the same time, in these exceptional cases, there is also an increased risk of having the robot arm perform an undesired action, e.g., damaging the robot arm or objects in its environment 82.

Accordingly, system 200 may use a generative model trained on the same training dataset as the machine learnable control model in order to determine a conformance value. The conformance value may be indicative of a conformance of the directional data instance to the training dataset, and may thus estimate a reliability of the machine learnable control model for the directional data instance. At least if the conformance value indicates sufficient conformance of the directional data instance to the training dataset and thus sufficient reliability, the control model may be applied to the directional data instance, and its output may be used to control the robot arm 300. If the conformance value does not indicate sufficient conformance, the controlling of the robot arm may be adapted to reduce the risk of performing an undesired action, e.g., by halting the robot arm, switching to a safe mode, assigning less importance to the output of the control model, etc.

Various detailed examples of coupling layers are described below. Generally, a generative model may comprise one or more such coupling layers.

The directional data instance may be generated based on a latent feature vector. Applying the generative model may comprise obtaining a latent feature vector and determining the synthetic directional data instance from the latent feature vector (e.g., deterministically or stochastically). The generative model may define a prior distribution according to which latent feature vectors are assumed to be distributed, and accordingly, random synthetic directional data instances may be generated by sampling the latent feature vector according to the prior distribution. Interestingly, it is also possible to adapt the latent feature vector in order to influence the directional data instance being generated, e.g., to control whether or not certain aspects are present in the generated directional data instance.

For example, the generative model may generate the directional data instance by:

obtaining a latent feature vector, e.g., sampling the latent feature vector according to a prior probability distribution;

applying an (e.g., trainable) initial part of the generative model to the latent feature vector to obtain an input intermediate representation including an input direction vector to the coupling layer;

applying the coupling layer to the input direction vector to obtain an output direction vector as part of an output intermediate representation, e.g., leaving parts of the input intermediate representation that are not input to the coupling layer unchanged;

applying a (e.g., trainable) final part of the generative model to the output intermediate representation to determine the directional data instance.

The initial part and final part of the generative model are optional: the coupling layer can also be applied directly to the latent feature vector and/or the output of the coupling layer may be directly comprised in the generated directional data instance. For example, the direction vector comprised in the directional data instance may be the output direction vector of the coupling layer or the output direction vector may provide multiple direction vectors comprised in the directional data instance.

Parts of the intermediate representation that are not input to the coupling layer may be used by the coupling layer as input to a parameter model to determine parameters of a circle transformation or a conditional rotation of the coupling layer.

The input and output intermediate representations can also represent data that does not represent a direction vector, e.g., that is not from a hypersphere or a manifold topologically equivalent to a hypersphere. For example, an intermediate representation may comprise data from the Euclidean manifold, data from the manifold of symmetric positive definite matrices, and/or data from the special Euclidean group, as can be used e.g. to represent a state of a robotic system. This other data can be transformed by other, non-coupling layers of the generative model as is conventional.

The generative model can comprise multiple coupling layers. For example, the output direction vector of one coupling layer may be used as input of another coupling layer, for example, in a sequence of at least three, at least five, or at least 10 coupling layers. Multiple coupling layers can be executed in parallel in the sense that they are applied to different parts of the same intermediate representation.

For example, in an embodiment, one or more subsequent coupling layers may be applied to a concatenation of multiple separate direction vectors, e.g., multiple 3D or 4D vectors, e.g., at least two, at least four or at least ten such separate direction vectors. Then, one or more subsequent coupling layers may be applied to each of the separate direction vectors separately. In this way, the generative model may first apply more global transformations to the overall directional data instance and then separately generate aspects of the individual direction vectors.

Training of the generative models described herein may be performed using stochastic approaches such as stochastic gradient descent, e.g., using the Adam optimizer as disclosed in Kingma and Ba, "Adam: A Method for Stochastic Optimization" (available at https://arxiv.org/abs/1412.6980 and incorporated herein by reference). The objective function to be optimized may comprise a sum of log-likelihoods of items of the training dataset being generated according to the generative model. As is conventional, such optimization methods may be heuristic and/or arrive at a local optimum. Training may be performed on an instance-by-instance basis or in batches, e.g., of at most or at least 64 or at most or at least 256 instances. It is beneficial from the point of view of efficiency of training to use a generative model which is amenable to gradient-based optimization, e.g., which is continuous and/or differentiable in its set of parameters.

For example, in an embodiment, the generative model may be a normalizing flow. The normalizing flow may be trained to approximate an intrinsic probability distribution of real-world data as represented by the training dataset. As an example, the MNIST dataset as is conventional consists of 28×28-pixel images of hand written digits and may thus correspond to an intrinsic probability distribution $p_X$ $(x_1, \ldots, x_{784})$ defined on $\mathbb{N}^{784} = X$. A pre-processing step, e.g., dequantization may be taken to deal with discrete data and to arrive at a continuous density. The distribution may be learned based on the change of variables formula. Let X be the domain of the space of data generated by the generative model; Z a latent space of latent feature vectors, e.g., with same dimensionality; $p_Z$ a probability distribution on Z and $f: \mapsto X$ (a mapping, e.g., a mapping that is differentiable and has a differentiable inverse. As is conventional, in a normalizing flow, the change-of-variables formula $$p_X(f(z)) = p_Z(z)|det J_f(z)|^{-1}$$

may provide an analytic form of the distribution of $f(z)$ with $z \sim p_Z$, e.g., the change-of-variables formula may represent how the distribution $p_Z$ changes under the action of $f$ on the latent space Z.

Thus, in normalizing flows and similar models, computing a likelihood of data being generated according to the model may comprise evaluating the determinant of the Jacobian of the inverse model, e.g., by evaluating the inverse of the determinant of the Jacobian of the model. This may in turn comprise evaluating the determinant of the Jacobian of the inverse coupling layer, e.g., by evaluating the inverse of the determinant of the Jacobian of the coupling layer. Interestingly, as also discussed elsewhere, components of the coupling layer as provided herein have a triangular structure, allowing these determinants to be computed in an efficient and numerically stable way. For example, the computational complexity of computing the determinant in some embodiments reduces from $\mathcal{O}(D^3)$ to $\mathcal{O}(D)$ because the determinant may be computed as a sum of diagonal elements.

The distribution $p_Z$ can be a probability distribution that has fixed parameters or is parametrized by parameters of the generative model, e.g., an uncorrelated Gaussian if Z is the Euclidean space, or a uniform distribution if Z is compact. The functions $f$ may be parameterized by various machine-learnable functions, e.g., one or more deep or other neural networks.

Accordingly, using a normalizing flow, complex distributions $p_X$ may be modelled based on base distributions $p_Z$.

In an embodiment of the present invention, the generative model is a SurVAE flow. A SurVAE flow is analogous to a normalizing flow but may comprise non-bijective layers, e.g., generative surjective, inference surjective, or stochastic layers. The coupling layer can be a bijective layer of the SurVAE flow, in which case it is applied similarly to in a normalizing flow. In particular, also in a SurVAE flow, computing a likelihood of data being generated may involve computing a determinant of a Jacobian of the coupling layer, as discussed above.

Generally, a direction vector comprised in directional data instance may be represented in various ways. For example, the direction vector may be represented by a set of Cartesian coordinates. For example, a direction vector representing a direction in 3-dimensional space may be represented as a 3-dimensional vector (x,y,z) with $x^2+y^2+z^2=1$, e.g., as point on the sphere $\mathbb{S}^2=\{(x,y,z)|x^2+y^2z^2=1\}$. Similarly, a direction in 2-dimensional space may be represented as a point on the circle $\mathbb{S}^1=\{(x,y)|x^2+y^2=1\}$. Generally, a direction vector corresponding to a direction in k dimensions may be represented as a point on the (k−1)-hypersphere $\mathbb{S}^{k-1}$.

The techniques described herein can be applied to higher-degree directional data, e.g., a direction vector representing a direction in at least 5, at least 10, or at least 20 dimensions. It is not needed to restrict the Cartesian coordinates to have a certain norm, e.g., the direction vector may in addition represent a magnitude, or vectors with different norms but the same direction component may be regarded as equivalent.

It is not necessary to use Cartesian coordinates; for example, the direction vector may be represented by one or more angles. In particular, a direction vector may represent an orientation in various ways. For example, as is conventional, an orientation in three-dimensional space may be represented as a point on the 3-sphere $\mathbb{S}^3=\{(x,y,z,a)|x^2+y^2+z^2+a^2=1\}$, as an element of the special orthogonal group SO(3), in an axis-angle representation, etc.

Figure 4:
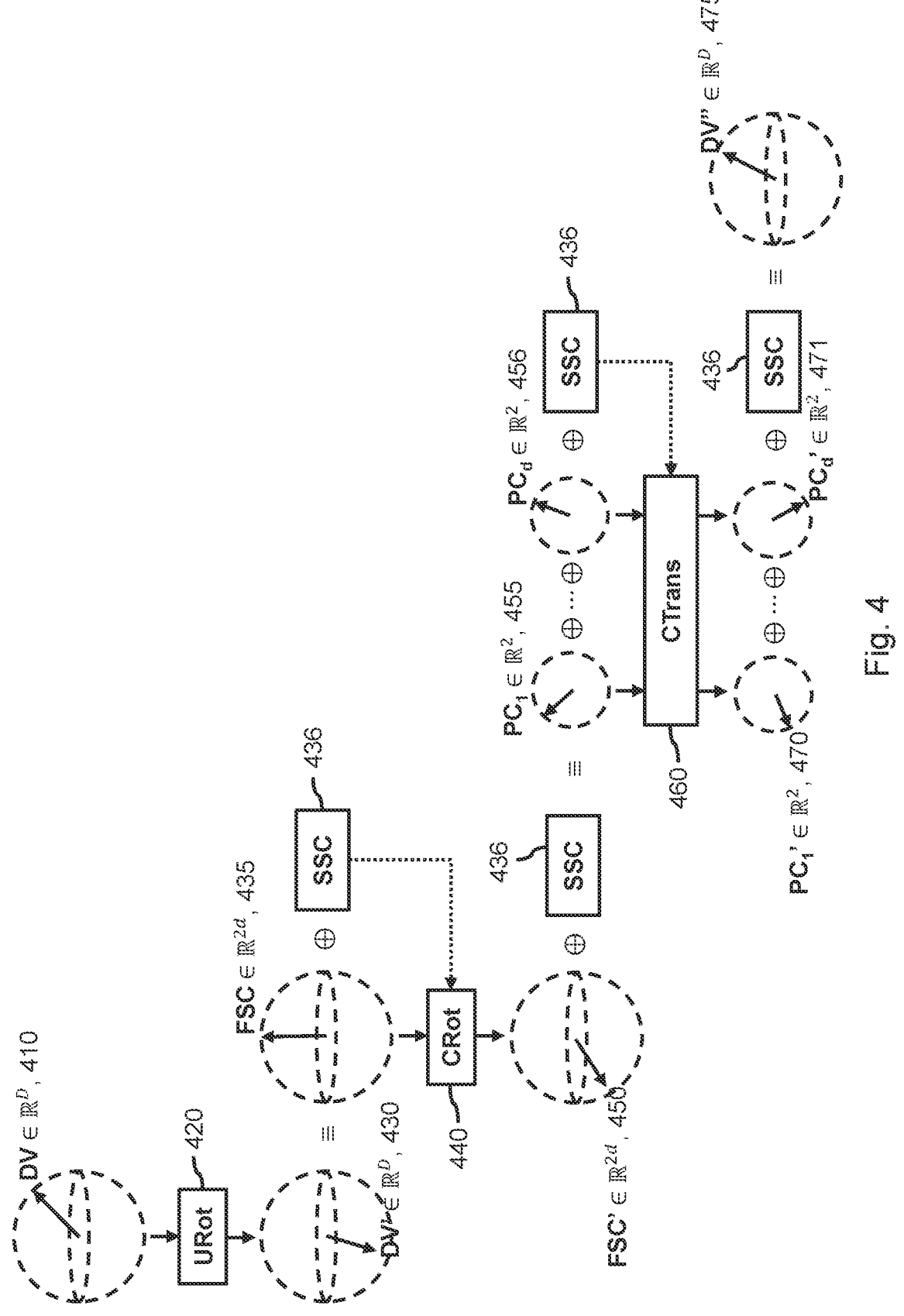
FIG. 4 shows a detailed example of a coupling layer, in accordance with an example embodiment of the present invention.

FIG. 4 shows a detailed, yet non-limiting, example of a coupling layer for use in a generative model as described herein. The coupling layer transforms an input direction vector DV, 410, to an output direction vector DV", 475.

As shown in this example, the input direction vector DV may represent a point on a hypersphere, for example, a point on a D−1 dimensional hypersphere $\mathbb{S}^{-1}$ may be represented as a D-dimensional vector with a certain norm, e.g., norm 1. The output direction vector DV" may be a point on that same hypersphere, e.g., a D-dimensional vector with the same norm. Throughout the description of this figure, it is assumed that the direction vector is represented by a set of Cartesian coordinates, although the actual representation used to store the direction vector can be different, e.g., at the beginning, end, and/or throughout the coupling layer, the direction vector may be represented as a set of angles, or as a combination of a vector and one or more angles. etc.

Typically, the input direction vector DV and the output direction vector DV" both have the same dimension. For example, the dimension of the input and/or output direction vector can be 3 for representing a direction in 3-dimensional space, 4 for representing an orientation in 3-dimensional space, corresponding to a unit quaternion, etc. The input and/or output direction vectors can also be a concatenation of one or more 2-dimensional direction vectors and/or one or more 3-dimensional direction vector and/or one or more 4-dimensional direction vectors, for example. The overall dimension of the input and/or output direction vector can for example be at least 10 or at least 20.

As shown in the figure, the coupling layer may involve a conditional and/or unconditional rotation, and a circle transformation being applied to the input direction vector. In this example, an unconditional rotation URot, 420, and a conditional rotation CRot, 440, are subsequently applied to the input direction vector DV, after which the circle transformation CTrans, 460, is applied to arrive at the output direction vector DV". However, it is also possible to skip one of the two rotations or to execute the unconditional rotation URot, the conditional rotation CRot, and the circle transformation CTrans in any other order than the one shown in the figure.

Unconditional rotation URot may rotate the direction vector DV according to parameters of the generative model to arrive at an updated direction vector DV', 430. The unconditional rotation typically preserves the dimensionality of direction vector DV. The unconditional rotation may be implemented by means of a number D of Householder reflections. Householder reflections on coordinates are an efficiently implementable, trainable, and invertible representation of the rotation operator. The unconditional rotation URot may be regarded as an arbitrary permutation of the dimensions of the data.

Mathematically, for example, a Householder reflection may be denoted as $$R_i = I - 2\frac{u_i u_i^T}{\|u_i\|^2},$$

where the parameter set $u=(u_i)_i^D$ is learned but fixed. Unconditional rotation URot may be implemented as $R=R_D \circ \ldots \circ R_i$, with the transformation being defined as:

$$R_u(x_{1:D})=x'_{1:D}$$

For example, the number D of Householder reflections can be equal to the dimension of the direction vector DV. This has the advantage that any rotation of the direction vector DV can be represented in this way. However, it is also possible to use fewer Householder reflections to decrease the number of parameters of the model.

Rotation based on Householder reflections allows the inverse of the unconditional rotation to be evaluated in an efficient and numerically stable manner. Since R is an orthogonal matrix, its inverse R may be obtained by transposition, e.g., $R^T x'=x$, and the transformation does not incur a volume change because $|\det R|=1$.

Conditional rotation CRot may rotate a subset FSC, 435, of coordinates of the direction vector DV', based on a second set SSC, 436, of coordinates of the direction vector DV', e.g., the remaining coordinates or a subset thereof. Accordingly, the conditional rotation CRot may result in a direction vector with updated coordinates FSC', 450, for the first subset of coordinates, while remaining coordinates, e.g., the second set of coordinates SSC, remain unchanged.

The parameters of the conditional rotation CRot may comprise model parameters of the generative model and/or parameters determined by applying a trained parameter model, e.g., a neural network or similar, to the second set of coordinates SSC.

Similarly to unconditional rotation URot, also conditional rotation CRot may be implemented by means of multiple Householder reflections. For example, the Householder reflections may have respective trained parameter models or may share a common parameter model. The number of Householder reflections here is preferably the same as the number of parameters of the first subset FSC, but can be less to save parameters. Denoting the parameter model $u=NN(x_{d+1:D})$, the conditional rotation CRot may be defined mathematically as:

$$R_u(x_{1:D})=x'_{1:D}.$$

The figure further shows circle transformation CTrans being applied to respective pairs of Cartesian coordinates (also referred to as "circle slices") of the direction vector. For example, the circle transformation CTrans may be applied to one, at least two, at least three, or at least five respective circle slices.

The figure shows pairs of coordinates PC1, 455, up to PCd, 456, being transformed into respective pairs of coordinates PC1', 470, up to PCd', 471. As shown in this figure, the pairs of coordinates are preferably the coordinates of the subset of coordinates FSC' that was transformed by the conditional rotation CRot, divided into pairs. Thus, the first set of coordinates FSC is in this case selected to contain an even number of coordinates. However, this is not necessary; it is also possible to take a subset of coordinates of the first set of coordinates FSC' and/or coordinates that were not transformed by the conditional rotation CRot (if using). There typically is also a set of coordinates to which no circle transformation is applied and that thus remain unchanged; in this case, this is the second set of coordinates SSC that was also not transformed by the conditional rotation CRot. The transformed pairs of coordinates PCi' and the unchanged coordinates SSC together may form the output direction vector DV".

Mathematically, for example, given a subset FSC' of coordinates of the direction vector, it may be observed that this subset $(x_{i_1}, \ldots, x_{i_n}) \in \mathbb{S}^D$ lies on a circle with radius $$x_{i_1}^2+ \ldots +x_{i_n}^2=r'=\sqrt{1-\Sigma_{k \neq i_1,\ldots,i_n} x_k^2} \leq 1$$

After splitting the coordinates into a first subset $x_{1:d}$, FSC', and a second subset SSC, $x_{d+1:D}$, where d is an even number, the first subset FSC' may be further split into independent pairs PCi of two coordinates, e.g., the following function may be applied:

$$_r \mathbb{S}^{d-1} \to _{r_1} \mathbb{S}^1 \times _{r_2} \mathbb{S}^1 \times \ldots \times _{r_{d/2}} \mathbb{S}^1$$

$$(x_1,x_2, \ldots ,x_d) \mapsto (x_1,x_2),(x_3,x_4), \ldots ,(x_{d-1},x_d)$$

where $r \mathbb{S}^1$ denotes a circle with radius r.

The circle transformation CTrans may act on a pair of coordinates PCi that represent a point on a circle with a certain radius, by transforming this point to a further point on that same circle, e.g., with the same radius. The transformation applied to the pair of coordinates PCi may be defined based on parameters of the generative model and/or by applying a trainable parameter determining model to further Cartesian coordinates. The parameters and/or parameter determining model are typically different for respective pairs of coordinates, although parameters can be shared between them. As shown in the figure, the further coordinates used may be (a subset of) parameters SSC that are not transformed by circle transformation CTrans. This has the advantage that the order in which different pairs of coordinates PCi are transformed does not matter, e.g., allowing parallelization, and that when inverting the circle transformation, the parameters can be based on these same unaffected parameters SSC.

The transformation applied to a pair of coordinates PCi can in general be any diffeomorphic map on the circle, as is conventional. Examples of such diffeomorphic maps are described in Rezende et al., "Normalizing Flows on Tori and Spheres", in particular section 2.1 (incorporated herein by reference).

In particular, a transformation on a pair of coordinates PCi may be applied by mapping the pair of coordinates PCi to an angle, applying a circle diffeomorphism to the angle, and mapping the resulting angle back to obtain the transformed pair of coordinates PCi'. For example, a circular Neural Spline Flow or a Möbius transformation may be used as described, e.g., in Rezende et al. Performing the transformation in terms of angles can help to ensure that the function is monotonically increasing and thus diffeomorphic. Moreover, the diffeomorphism applied to the circle can be defined as a combination of other diffeomorphisms $\{f\}_k^K$, e.g., by function composition $f=f_K \circ \ldots f_1$ or by taking a convex combination $f=\Sigma_i \rho_i f_i$, e.g., with trainable parameters $\rho_i$. By taking functions defined on angles, it may be ensured that the convex combination is still a diffeomorphism.

Mathematically, for example, the transformation of a pair of coordinates may be implemented as:

$$f_i=T^{-1} \circ CircleFlow \circ T : _{r_i} \mathbb{S}^1 \to _{r_i} \mathbb{S}^1$$

$$f_i:(x_{k_i},x_{l_i}) \mapsto T(x_{k_i},x_{l_i})=\theta \mapsto \theta'= \\ Flow(\theta | x_{d+1:D+1}, r_i) \mapsto T^{-1}(\theta',r)=(x'_{k_i},x'_{l_i})$$

where $$T: \mathbb{S}^1 \subset \mathbb{R}^2 \to [0,2\pi]$$

is a bijection that maps between Cartesian coordinates of $\mathbb{S}^1$ embedded in $\mathbb{R}^2$ and its parametrized coordinate, e.g., $$T:(x,y) \mapsto \arctan 2(y,x) \bmod 2\pi \text{ and } T^{-1}:(\theta,r) \mapsto (r\cos\theta, r\sin\theta).$$

For example, CircleFlow:$r_i\mathbb{S}^1 \to r_i\mathbb{S}^1$ can be a Neural Spine Flow or a Möbius transformation, or another circle diffeomorphism.

It may be noted, e.g., for computing log-likelihoods, that the volume change inflicted by the switch between the parametrized angle and Cartesian coordinates solely depends on the radius of the circle slice with $$\det J_T = \frac{1}{r}.$$

Thus, the mapping from and to angles may cancel out each other, since the radius does not change under the flow transformation. The volume changes due to the flow are conventional and are efficiently computable. Interestingly, because circle slices may be independently transformed, the Jacobian of the overall transformation may be triangular and may thus be computed in an efficient and numerically stable way.

Interestingly, using the coupling layer presented herein, it is possible both to efficiently compute output direction vector DV″ from input direction vector DV in the generative direction; and to efficiently compute the input direction vector DV from the output direction vector DV″ in the inverse, inference direction. In particular, computing the inverse may be combined with the computation of a likelihood, e.g., a log-likelihood, of directional data being generated according to the generative model. For example, computing this likelihood may involve computing a determinant of the Jacobian of the coupling layer as described herein.

In particular, in the example shown in the figure, the output direction vector DV″ may be divided into pairs of Cartesian coordinates PCi′ and a second set of coordinates SSC. Respective pairs of Cartesian coordinates PCi′ may be transformed by applying an inverse of the circle transformation CTrans to arrive at pairs of Cartesian coordinates PCi, while the second set of coordinates SSC may remain unchanged. Interestingly, the parameters of the circle transformation CTrans may be based on model parameters and/or the second set of parameters SSC, e.g., they can be computed either from the inputs to the circle transformation (in the generative direction) or from its out puts (in the inference direction) with the same result. Moreover, the order in which respective pairs PCi′ are transformed by the inverse may not matter and the inversion can thus be parallelized.

Given the pairs of coordinates PCi and the second set of coordinates SSC, an inverse of the conditional rotation CRot may be applied. The parameters of the conditional rotation may be determined based on model parameters and/or the second set of coordinates unaffected by the conditional rotation CRot, so that again the parameters can be determined in the generative and inference direction in the same way. Based on the parameters, an inverse rotation can be applied to the combined pairs of coordinates FSC′ to arrive at first set of coordinates FSC. An inverse of the unconditional rotation URot can then be applied to the combination of the first set of coordinates FSC and the second set of coordinates SSC to arrive at the input direction vector DV.

As the skilled person understands, this inversion can be adapted to variations of the coupling layer shown in the figure where, e.g., the order of the transformations URot, CRot, CTrans is different; one of the rotations URot, CRot is skipped; or the sets of unaffected coordinates differ between the conditional rotation CRot and the circle transformation CTrans.

Below, a detailed pseudocode example is given of an algorithm that may be used to evaluate the coupling layer shown in this figure in the generative direction.

---

Algorithm.

Input: $(x_1, \ldots, x_D)$
$x_{1:D} \leftarrow R_\psi(x_1, \ldots, x_D)$ // rotate unconditionally, e.g., using Rotate module below
$d \leftarrow \text{round\_up\_to\_even}(D/2)$
$(x_1, \ldots, x_d), (x_{d+1}, \ldots, x_D) \leftarrow \text{split } x_{1:D}{}^1 \text{ at } d$
$x_{1:d} \leftarrow R_\psi(x_{1:d}|x_{d+1:D})$ // rotate conditionally, e.g., using Rotate module below
for all distinct pairs $(x_i, x_j)$ in $(x_{1:d})$ do
  $\theta \leftarrow T(x_i, x_j) = \arctan 2(x_j, x_i) \bmod 2\pi$
  $r \leftarrow x_i^2 + x_j^2$
  $\theta' = \text{Flow}(\theta|x_{d+1:D}, r)$ // e.g., Flow E ∈ {Moebius Flow, NSF}
  $(x_i', x_j') = T^{-1}(\theta', r) = (r\cos\theta', r\sin\theta')$
return $(z_1, \ldots, z_D) = (x_1', \ldots, x_d') \cup (x_{d+1}, \ldots, x_D)$ // return concatenation

Rotate module

Input: $(x_1, \ldots, x_D)$, conditional_flag // flag indicates conditional/unconditional rotation
if conditional_flag then // get params $\psi$ with shape (D, D)
  $\psi \leftarrow NN(x_{d:D})$
else
  $\psi \leftarrow D \times D$ model parameters
$R \leftarrow$ initialize as $D \times D$ identity matrix.
for each column vector u in $\psi$ do $$u \leftarrow \frac{u}{\|u\|}$$

$R_0 \leftarrow I - 2uu^T$
$R \leftarrow R \cdot R_0$
return $R \cdot (x_1, \ldots, x_D)$

Moebius Flow

Input: $(\theta, r)$, nr_centers // nr_centers indicates number of convex combinations
$w \leftarrow NN(x_{d+1:D})$ // get params w with shape (2, nr_centers)

$$w_i = \frac{0.99r}{1 + \|w_i\|} \quad\quad \text{// norm each } w_i \text{ of shape } (2, \cdot)$$

$$\text{return (out, } ldj) = \frac{1}{\text{nr\_centers}} \sum_i MoebTransf(\theta|w_i)$$

---

FIG. 5$a$ shows a detailed example of applying a coupling layer to two four-dimensional direction vectors, e.g. representing orientations of physical objects.

In this example, the input direction vector to which the coupling layer is applied, is an 8-dimensional input direction vector that is the concatenation of two four-dimensional direction vectors DV1, 510, and DV2, 511. In this example, the first direction vector DV1 is transformed while the second direction vector DV2 remains unchanged but can be used to parameterize the transformations of the first direction vector DV1.

In this coupling layer, a conditional rotation CRot, 540, may rotate the Cartesian coordinates of the first direction vector DV1, resulting in updated first direction vector DV1′. The conditional rotation CRot may be as described with respect to FIG. 4, e.g., the conditional rotation may be parameterized based on parameters of the generative model and/or based on the second direction vector DV2.

The resulting updated direction vector DV1′ may then be divided into two circle slices PC1, 555, PC2, 556, of two Cartesian coordinates each. A circle transformation CTrans, 560, may be applied to the respective circle slices to obtain respective output points PC1', 570, PC2', 571, with the same radius as input circle slides PCi. The circle transformation CTrans may be as described with respect to FIG. 4, and may in particular be parameterized by parameters of the generative model and/or by the second direction vector DV2 to which no conditional rotation or circle transformation is applied.

As shown in the figure, the output points PC1', PC2' may together form a four-dimensional direction vector DV1", e.g., a direction vector lying on the same hypersphere as original first direction vector DV1. The updated first direction vector DV1" and the original second direction vector DV2 may together form an 8-dimensional output direction vector of the coupling layer, e.g., lying on the same hypersphere as the input direction vector formed by DV1 and DV2.

Interestingly, in this example, not only the input direction vector may be preserved in a norm-preserving way, but also the first and second direction vectors DV1, DV2, may preserve their norm. This is advantageous if they represent distinct directional quantities, although also in such cases it is not absolutely necessary for a coupling layer to guarantee that norms of separate direction vectors are preserved, e.g., also without such guarantees, conformance checking can give meaningful results.

As the skilled person understands, this example can be generalized, e.g., to the case where multiple 4-dimensional direction vectors are used to parameterize the transformation of the first direction vector DV1, and/or where the first and second direction vectors DVi have other dimensions.

Figures 5A, 5B:
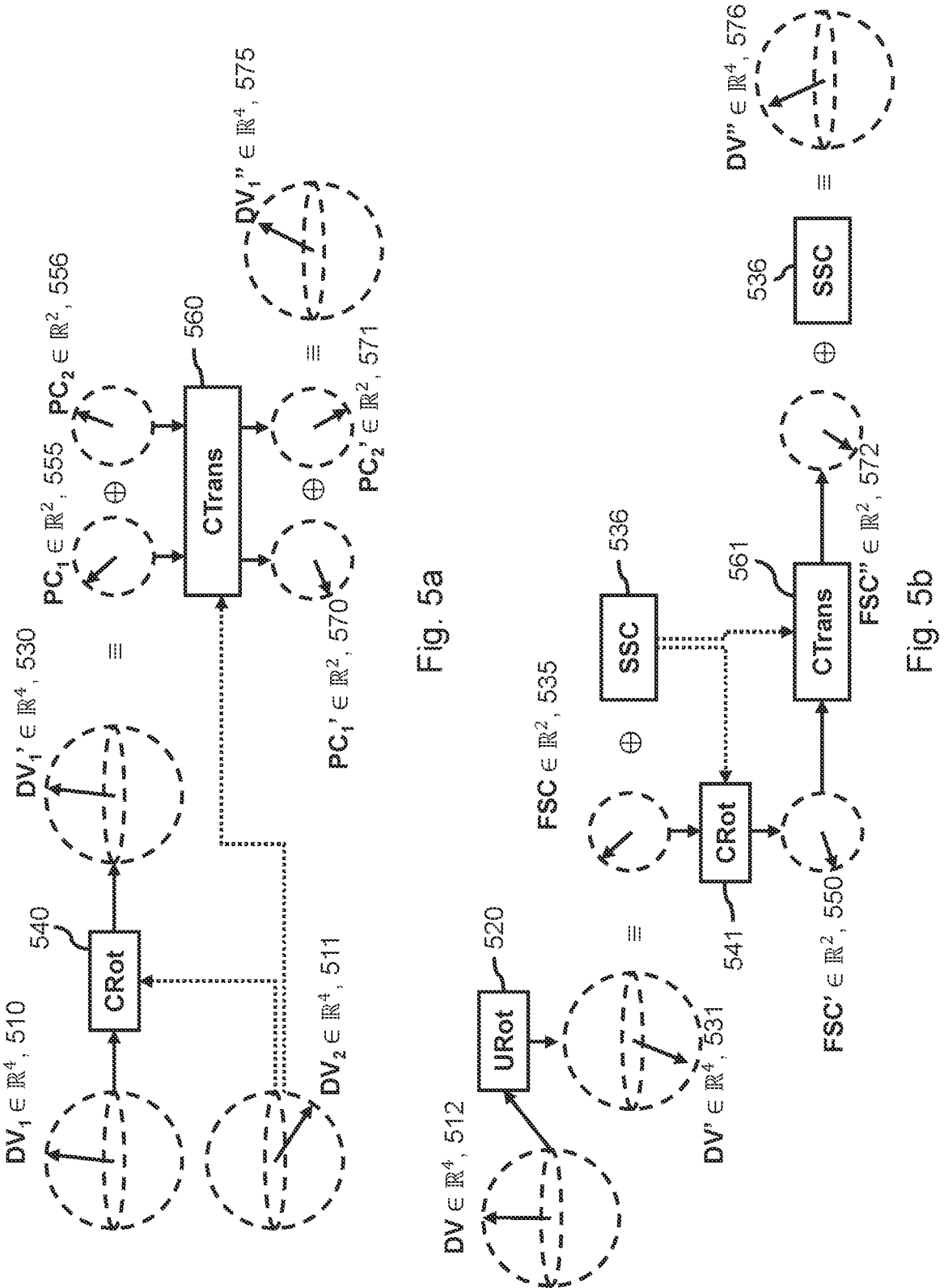
FIG. 5a shows a detailed example of applying a coupling layer to two four-dimensional direction vectors, e.g. representing orientations of physical objects, in accordance with an example embodiment of the present invention.
FIG. 5b shows a detailed example of applying a coupling layer to a direction vector, e.g., representing an orientation of a physical object, in accordance with an example embodiment of the present invention.

FIG. 5b shows a detailed example of applying a coupling layer. In this example, the input direction vector of the coupling layer is a four-dimensional vector DV, e.g., representing an orientation of a physical object. The coupling layer may be norm-preserving, e.g., an input direction vector on a 4-dimensional hypersphere may be mapped to an output direction vector on the same 4-dimensional hypersphere.

An unconditional rotation URot, 520, may be applied to the input direction vector DV to obtain an updated direction vector DV', 531. For example, the unconditional rotation URot may be as described with respect to FIG. 4.

The updated direction vector DV' may be divided into a first set of coordinates FSC, 535, being a pair of coordinates representing a circle slice, and a second set of coordinates SSC, 536, e.g., the remaining two coordinates. The first set of coordinates FSC may then be transformed by a conditional rotation CRot, 541, leading to an updated first circle slice FSC', 550. The conditional rotation may be as in FIG. 4, and may be parameterized by the second set of coordinates SSC.

The updated first circle slice FSC' may then be transformed by a circle transformation CTrans, 561, to obtain circle slice FSC". The circle transformation CTrans may be as in FIG. 4 and may be parameterized by the second set of coordinates SSC. The circle slice determined by circle transformation CTrans and the second set of coordinates SSC may together form the output direction vector DV" of the coupling layer.

As the skilled person understands, many variations of this example are possible, e.g., the unconditional rotation URot or the conditional rotation CRot may be skipped, the operations URot, CRot, CTrans may be performed in a different order, etc.

Figures 6, 7, 8:
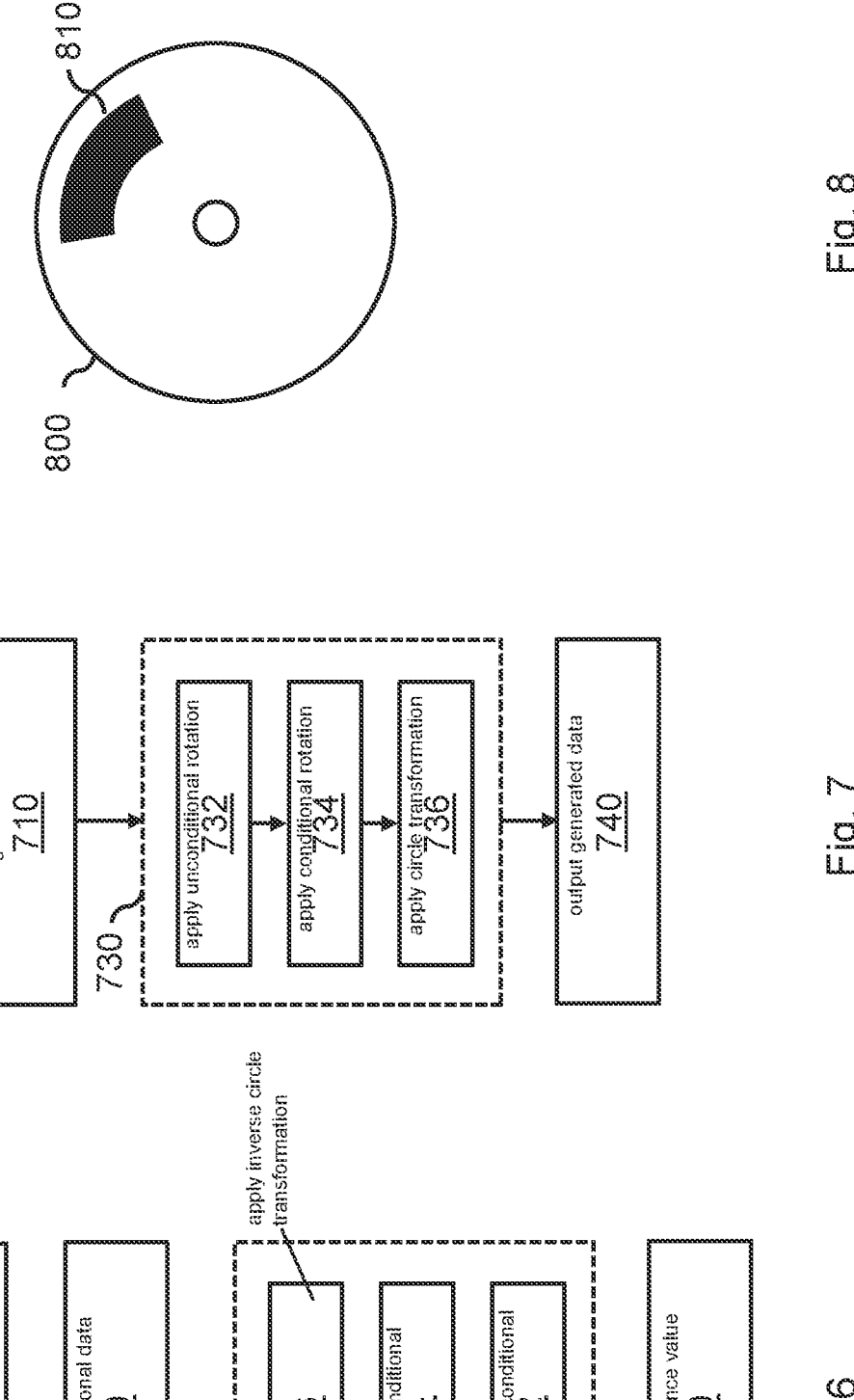
FIG. 6 shows a computer-implemented method of estimating reliability, in accordance with an example embodiment of the present invention.
FIG. 7 shows a computer-implemented method of generating a synthetic directional data instance, in accordance with an example embodiment of the present invention.
FIG. 8 shows a computer-readable medium comprising data, in accordance with an example embodiment of the present invention.

FIG. 6 shows a block-diagram of computer-implemented method 600 of determining conformance of a directional data instance to a dataset. For example, the directional data instance may be a model input for a machine learnable control model based on which the control model may infer control data for controlling a computer-controlled system interacting with an environment. Conformance to the training dataset of the machine learnable control model may in this case be used as an estimate of a reliability of the control data. The method 600 may correspond to an operation of the system 100 of FIG. 1, or the system 200 of FIG. 2. However, this is not a limitation, in that the method 600 may also be performed using another system, apparatus or device.

The method 600 may comprise, in an operation titled "ACCESS GENERATIVE MODEL", accessing 610 model data representing a generative model. The generative model may be trained, e.g., previously or as part of method 600, to generate synthetic directional data representative of the dataset.

The method 600 may comprise, in an operation titled "OBTAIN DIRECTIONAL DATA", obtaining 620 the directional data instance. The directional data may comprise at least one direction vector. The direction vector may be associated with a physical object, e.g., a component of the computer-controlled system or an object in its environment. The direction vector may be extracted, e.g., previously or as part of method 600, from sensor data representing the physical object.

The method 600 may comprise, in an operation titled "APPLY INVERSE GENERATIVE MODEL", applying 630 an inverse of the generative model to the directional data instance to determine a likelihood of the directional data instance being generated according to the generative model. Method 600 may further comprise, in an operation titled "DETERMINE CONFORMANCE VALUE", determining 640 a conformance value based on the determined likelihood. The conformance value may be indicative of a conformance of the directional data to the dataset, e.g., the conformance value may be a reliability measure for control data to be inferred by the machine learnable model. The generative model may comprise a coupling layer transforming an input direction vector to an output direction vector.

The coupling layer may comprise a circle transformation and one or more of an unconditional rotation and a conditional rotation.

The operation 630 may comprising applying an inverse of the coupling layer.

In order to apply the inverse of the coupling layer, the method 600 may comprise, in an operation titled "APPLY INVERSE CIRCLE TRANSFORMATION", applying 636 an inverse of a circle transformation. Said inverse may be applied to a pair of Cartesian coordinates representing a point on a circle. Said inverse may transform said point to a further point on the circle. The circle transformation may be defined based on parameters of the generative model and/or further Cartesian coordinates.

In order to apply the inverse of the coupling layer, the method 600 may further comprise, in an operation titled "APPLY INVERSE UNCONDITIONAL ROTATION", applying 632 an inverse of an unconditional rotation. Instead of or in addition to operation 632, the method 600 may comprise, in an operation titled "APPLY INVERSE CONDITIONAL ROTATION", applying 634 an inverse of a conditional rotation. The inverse of the unconditional rotation may rotate a direction vector according to parameters of the generative model. The inverse of the conditional rotation may rotate a first set of Cartesian coordinates based on a second set of Cartesian coordinates.

FIG. 7 shows a block-diagram of computer-implemented method 700 of generating a synthetic directional data instance according to a generative model. The synthetic directional data instance may comprise at least one direction vector associated with a physical object. The method 700 may correspond to an operation of the system 100 of FIG. 1. However, this is not a limitation, in that the method 700 may also be performed using another system, apparatus or device.

The method 700 may comprise, in an operation titled "ACCESS GENERATIVE MODEL", accessing 710 model data representing the generative model. The generative model may be trained, e.g., previously or as part of method 700, to generate directional data instances representative of a training dataset.

The method 700 may comprise, in an operation titled "APPLY GENERATIVE MODEL", applying 730 the generative model. Operation 730 may comprise applying the coupling layer to an input direction vector. The method 700 may further comprise, in an operation titled "OUTPUT GENERATED DATA", outputting 740 the generated synthetic directional data instance.

The generative model may comprise a coupling layer transforming an input direction vector to an output direction vector. The coupling layer may comprise a circle transformation and one or more of an unconditional rotation and a conditional rotation.

To apply the coupling layer, the method 700 may comprise, in an operation titled "APPLY UNCONDITIONAL ROTATION", applying 732 the unconditional rotation. Instead of or in addition to operation 732, the method 700 may comprise, in an operation titled "APPLY CONDITIONAL ROTATION", applying 734 the conditional rotation. The unconditional rotation may rotate a direction vector according to parameters of the generative model. The conditional rotation may rotate a first set of Cartesian coordinates based on a second set of Cartesian coordinates.

To apply the coupling layer, the method 700 may further comprise, in an operation titled "APPLY CIRCLE TRANSFORMATION", applying 736 a circle transformation to a pair of Cartesian coordinates representing a point on a circle. Said transformation may transform said point to a further point on the circle. The circle transformation may be defined based on parameters of the generative model and/or further Cartesian coordinates.

It will be appreciated that, in general, the operations of method 600 of FIG. 6 and method 700 of FIG. 7 may be performed in any suitable order, e.g., consecutively, simultaneously, or a combination thereof, subject to, where applicable, a particular order being necessitated, e.g., by input/output relations. Some or all of the methods may also be combined, e.g., method 700 of using the generative model may be applied subsequently to this trained model being trained according to method 600, or method 600 may be used first to train the generative model on a training dataset and subsequently to determine conformance of an obtained directional data instance that is not from the training dataset.

The method(s) may be implemented on a computer as a computer implemented method, as dedicated hardware, or as a combination of both. As also illustrated in FIG. 8, instructions for the computer, e.g., executable code, may be stored on a computer readable medium 800, e.g., in the form of a series 810 of machine-readable physical marks and/or as a series of elements having different electrical, e.g., magnetic, or optical properties or values. The executable code may be stored in a transitory or non-transitory manner. Examples of computer readable mediums include memory devices, optical storage devices, integrated circuits, servers, online software, etc. FIG. 8 shows an optical disc 800. Alternatively, the computer readable medium 800 may comprise transitory or non-transitory model data 810 representing a generative model as described herein, e.g., comprising parameters of one or more coupling layers.

Examples, embodiments or optional features, whether indicated as non-limiting or not, are not to be understood as limiting the present invention.

It should be noted that the above-mentioned embodiments illustrate rather than limit the present invention, and that those skilled in the art will be able to design many alternative embodiments.

Herein, any reference signs placed between parentheses shall not be construed as limiting. Use of the verb "comprise" and its conjugations does not exclude the presence of elements or steps other than those stated. The article "a" or "an" preceding an element does not exclude the presence of a plurality of such elements. Expressions such as "at least one of" when preceding a list or group of elements represent a selection of all or of any subset of elements from the list or group. For example, the expression, "at least one of A, B, and C" should be understood as including only A, only B, only C, both A and B, both A and C, both B and C, or all of A, B, and C. The present invention may be implemented by means of hardware comprising several distinct elements, and by means of a suitably programmed computer. In a device described as including several means, several of these means may be embodied by one and the same item of hardware. The mere fact that certain measures are described separately does not indicate that a combination of these measures cannot be used to advantage.

What is claimed is:

1. A computer-implemented method of estimating a reliability of control data for a computer-controlled system interacting with an environment, wherein the control data is inferred from a model input by a machine learnable control model which is trained on a training dataset, the method comprising the following steps:

accessing model data representing a generative model, wherein the generative model is trained to generate synthetic model inputs representative of the training dataset of the control model;

obtaining the model input, wherein the model input includes at least one direction vector which is extracted from sensor data and which is associated with a component of the computer-controlled system or an object in the environment;

applying an inverse of the generative model to the model input to determine a likelihood of the model input being generated according to the generative model; and determining a reliability measure for the control data of the machine learnable model based on the likelihood, wherein the generative model includes a coupling layer determining an input direction vector from an output direction vector in an inference direction and determining the output direction vector from the input direction vector in a generative direction, the coupling layer including a circle transformation and one or more of an unconditional rotation and a conditional rotation, wherein:

the circle transformation transforms a pair of Cartesian coordinates representing a point on a circle to a further point on the circle, wherein the circle transformation is defined based on parameters of the generative model and/or further Cartesian coordinates;

the unconditional rotation rotates a direction vector according to the parameters of the generative model; and the conditional rotation rotates a first set of Cartesian coordinates based on a second set of Cartesian coordinates, wherein when the reliability measure does not indicate a predetermined reliability:

not using the control data to control the computer-controlled system, controlling the system in a safe mode, or raising an alert.

2. The method of claim 1, wherein the circle transformation includes:

mapping the pair of Cartesian coordinates to an angle, applying a circle diffeomorphism to the angle, and mapping the angle to the further Cartesian coordinates.

3. The method of claim 2, further comprising determining parameters of the circle diffeomorphism by applying a trained parameter model to a size of the circle and Cartesian coordinates to which no circle transformation is applied.

4. The method of claim 1, wherein the unconditional rotation and/or the conditional rotation each include multiple Householder reflections.

5. The method of claim 1, wherein the direction vector corresponds to a unit quaternion representing an orientation of the component or object, and wherein the output direction vector corresponds to one or more unit quaternions.

6. The method of claim 1, further comprising, at least if the reliability measure indicates a reliability, applying the control model to the model input and using the control data inferred by the control model to control the computer-controlled system.

7. The method of claim 6, wherein the direction vector represents an orientation of a link of a robot arm, the control data being used to control the robot arm.

8. The method of claim 1, further comprising training the generative model by obtaining the model input from the training dataset and maximizing the determined likelihood.

9. A computer-implemented method of generating a synthetic directional data instance according to a generative model, the synthetic directional data instance including at least one direction vector associated with a physical object, the method comprising the following steps:

accessing model data representing the generative model, wherein the generative model is trained to generate synthetic directional data instances representative of a training dataset;

applying the generative model to generate the synthetic directional data instance; and outputting the generated synthetic directional data instance, wherein the generative model includes a coupling layer determining an input direction vector from an output direction vector in an inference direction and determining the output direction vector from the input direction vector in a generative direction, the coupling layer including a circle transformation and one or more of an unconditional rotation and a conditional rotation, wherein:

the circle transformation transforms a pair of Cartesian coordinates representing a point on a circle to a further point on the circle, wherein the circle transformation is defined based on parameters of the generative model and/or further Cartesian coordinates;

the unconditional rotation rotates a direction vector according to the parameters of the generative model; and the conditional rotation rotates a first set of Cartesian coordinates based on a second set of Cartesian coordinates, wherein when the reliability measure does not indicate a predetermined reliability:

not using the control data to control the computer-controlled system, controlling the system in a safe mode, or raising an alert.

10. The method of claim 9, wherein the training dataset comprises training model inputs of a machine learnable control model for a computer-controlled system interacting with an environment, wherein a direction vector of a training model input is extracted from sensor data and is associated with a component of the computer-controlled system or an object in the environment, and wherein the method further comprises applying the generative model repeatedly to obtain multiple synthetic model inputs, and training the control model to infer control data for the computer-controlled system using the multiple synthetic model inputs as training and/or test data.

11. The method of claim 10, further comprising obtaining a model input for the control model and applying the control model to the model input to infer control data for the computer-controlled system.

12. The method of claim 9, wherein the generative model is configured to generate a synthetic directional data instance representing a candidate protein conformation, the direction vector representing an orientation or a direction of a backbone component of the protein.

13. A non-transitory computer-readable medium on which is stored instructions for estimating a reliability of control data for a computer-controlled system interacting with an environment, wherein the control data is inferred from a model input by a machine learnable control model which is trained on a training dataset, the instructions, when executed by a processor system, causing the processor system to perform the following steps:

accessing model data representing a generative model, wherein the generative model is trained to generate synthetic model inputs representative of the training dataset of the control model;

obtaining the model input, wherein the model input includes at least one direction vector which is extracted from sensor data and which is associated with a component of the computer-controlled system or an object in the environment;

applying an inverse of the generative model to the model input to determine a likelihood of the model input being generated according to the generative model, and determining a reliability measure for the control data of the machine learnable model based on the likelihood, wherein the generative model includes a coupling layer determining an input direction vector from an output direction vector in an inference direction and determining the output direction vector from the input direction vector in a generative direction, the coupling layer including a circle transformation and one or more of an unconditional rotation and a conditional rotation, wherein:

the circle transformation transforms a pair of Cartesian coordinates representing a point on a circle to a further point on the circle, wherein the circle transformation is defined based on parameters of the generative model and/or further Cartesian coordinates;

the unconditional rotation rotates a direction vector according to the parameters of the generative model; and the conditional rotation rotates a first set of Cartesian coordinates based on a second set of Cartesian coordinates, wherein when the reliability measure does not indicate a predetermined reliability:

not using the control data to control the computer-controlled system, controlling the system in a safe mode, or raising an alert.

* * * * *